Oct. 2, 1951
N. GRILLO
HYBRID TEA ROSE PLANT
Filed Feb. 15, 1950
Plant Pat. 1,043
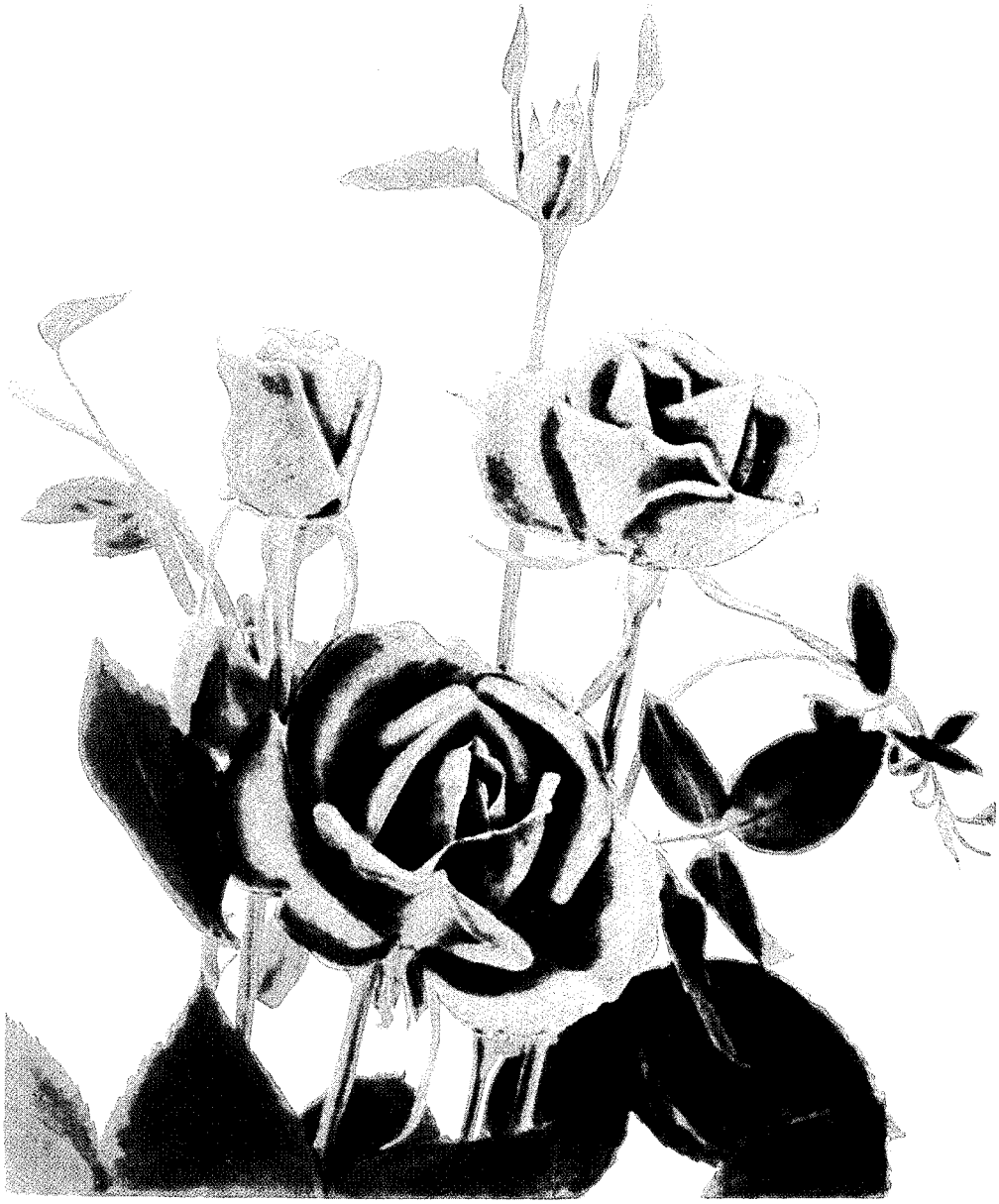
INVENTOR
Nicholas Grillo
By Orville M. Kile
Plant Pat. Agt.

Patented Oct. 2, 1951

Plant Pat. 1,043

UNITED STATES PATENT OFFICE 1,043

HYBRID TEA ROSE PLANT

Nicholas Grillo, Milldale, Conn.

Application February 15, 1950, Serial No. 144,346

1 Claim. (Cl. 47—61)

My present invention relates to an improved variety of hybrid tea rose plant. It is a sport of the variety Jewel (Plant Patent #367), discovered and developed in my gardens in the course of my regular horticultural practices. It resembles its parent in many ways, but differs principally in the following points:

1. My new variety has a larger bud than its parent.
2. It is a more abundant bloomer.
3. Its flower stems are longer.
4. The bloom has more large petals.
5. The bloom is slightly darker red.
6. Foliage is slightly lighter in color.

I have asexually reproduced this new variety by means of budding, at my greenhouses in Milldale, Connecticut, and its distinguishing features have proved to be permanent.

The accompanying illustrations show in approximately their true colors, four specimens of the bloom of my new variety in various stages of opening, together with portions of the stem and foliage.

In the following detailed description, color plate numbers refer to Ridgway's Color Standards and Nomenclature. Other color terminology is in accordance with the usual dictionary meaning.

*The plant*

Growth habit: Vigorous, upright bush.

Blooming habit: Continuous bloomer, producing even more flowers than its parent which is known as an abundant producer of bloom.

Foliage:

*Quantity.*—Abundant.

*Leaflets.*—Usually 3 to 5, occasionally 7.

*Size.*—Medium, with terminal leaflet averaging 3 inches long by 1½ inches wide. Terminal leaflet is considerably longer than lateral ones.

*Color.*—A little lighter green than the foliage of its parent.

*Shape.*—Long oval with acuminate apex. Edge sharply, finely and evenly serrated.

*Texture.*—Heavy and smooth.

*Rachis.*—Grooved above. Under side mostly smooth.

*Stipules.*—Small; clinging; sharp; points extend outward.

Stems: Strong; very long; light green with some bronze overlay.

Thorns: Light green, sometimes tinged with pink; downward-pointing. Few appear on upper part of stem but many on lower portion.

Sepals: Of varying lengths; at least two on each bloom are inclined to be foliaceous; reflex early, clasping stem.

*The flower*

Bud:

*Shape.*—Cone shaped when small, becoming long-pointed.

*Color.*—Between Amaranth Purple (Plate XII) and Carmine (Plate I).

*Size.*—Large.

*Opening.*—Perfect and slow. Does not bullhead.

*Peduncle.*—Smooth except for a few very fine spines; strong; relatively short (4 or 5 inches).

Bloom:

*Borne.*—Singly.

*Size.*—Medium to large. Averages about 4½ to 5 inches in diameter.

*Form.*—High-centered, which form it retains until the flower is very old, when it finally opens wide to reveal the stamens. Petals reflex slightly in early stages and a great deal in fully open stage.

*Color.*—Approximately the same as that of the bud.

*Petalage.*—In the winter months about 40 to 45.

Petals:

*Appearance.*—Velvety on upper surface.

*Texture.*—Heavy.

*Shape.*—Broadly obovate.

*Size.*—Outer petals measure 1¾ to 2 inches in each direction and are very much larger than the inner petals.

*Fragrance.*—Pleasing and lasting.

*Behavior.*—Clinging.

Longevity: Excellent, with no apparent change in color.

Reproductive organs:

*Pistils.*—Many; bunched; uneven in length. *Styles*—white. *Stigmas*—pink, tipped with yellow.

*Stamens.*—Few; surround pistils; uneven lengths. *Filaments*—Rose Red (Pl. XII). *Anthers*—Light Orange Yellow (Pl. III).

Having thus disclosed my discovery, I claim:

The new and distinct variety of hybrid tea rose plant, substantially as herein shown and described, characterized particularly by its prolific production of blooms; its long, strong stems; its large bud; its plentiful foliage which is lighter in color than that of its parents; and its large blooms possessing excellent keeping qualities as well as unfading and equally distributed dark red color which is a little darker and more uniform than that of its parent.

NICHOLAS GRILLO.

REFERENCES CITED

The following references are of record in the file of this patent:

UNITED STATES PATENTS

| Number | Name | Date |
|---|---|---|
| Pl. Pt. 367 | Grillo | Mar. 5, 1940 |